United States Patent [19]

Resconi et al.

[11] Patent Number: 5,892,077
[45] Date of Patent: Apr. 6, 1999

[54] PROCESS FOR MODIFYING THE RAC/MESO RATIO IN A METALLOCENE COMPOUND

[75] Inventors: Luigi Resconi; Davide Balboni, both of Ferrara, Italy

[73] Assignee: Montell Technology Company BV, Netherlands

[21] Appl. No.: 895,014

[22] Filed: Jul. 16, 1997

[30] Foreign Application Priority Data

Jul. 16, 1996 [EP] European Pat. Off. .............. 96202011

[51] Int. Cl.⁶ ................................ C07F 17/00; C07F 7/00
[52] U.S. Cl. .................. 556/11; 556/20; 556/43; 556/45; 534/15; 526/160; 526/943; 502/152; 502/162
[58] Field of Search .................. 556/11, 20, 43, 556/45; 534/15; 526/943; 502/152, 162

[56] References Cited

U.S. PATENT DOCUMENTS

| | | | |
|---|---|---|---|
| 4,769,510 | 9/1988 | Kaminsky | 585/512 |
| 5,302,733 | 4/1994 | Diefenbach et al. | 556/11 |
| 5,556,997 | 9/1996 | Strickler et al. | 556/11 |
| 5,597,935 | 1/1997 | Jordan et al. | 556/11 |
| 5,672,668 | 9/1997 | Winter et al. | 526/127 |

FOREIGN PATENT DOCUMENTS

| | | |
|---|---|---|
| 0 643 078 A2 | 3/1995 | European Pat. Off. . |
| 0 722 950 | 1/1996 | European Pat. Off. . |
| 19525184 A1 | 1/1997 | Germany . |
| WO 95/35333 | 12/1995 | WIPO . |
| WO 96/19488 | 6/1996 | WIPO . |

*Primary Examiner*—Porfirio Nazario-Gonzalez
*Attorney, Agent, or Firm*—Bryan Cave LLP

[57] ABSTRACT

It is possible to modify the rac/meso ratio of a rac/meso mixture in a stereorigid, bridged metallocene compound by subjecting a rac/meso isomeric mixture directly obtained from the synthesis to selective decomposition of the undesired isomer in the presence of compounds having either acidic hydrogen atoms or reactive halogen atoms. This process allows to prepare chiral metallocenes in their pure racemic or meso isomeric form.

20 Claims, No Drawings

PROCESS FOR MODIFYING THE RAC/MESO RATIO IN A METALLOCENE COMPOUND

The present invention relates to a process for the modification of the rac/meso ratio of a rac/meso mixture in a stereorigid metallocene compound.

Stereorigid metallocene compounds having two substituted cyclopentadienyl ligands joined by means of a bridging group which gives stereo-rigidity to the molecule are known to be stereospecific catalyst components for the preparation of isotactic polyolefins. These metallocenes can exist in two configurations, that is the racemic and the meso isomeric form. As the chiral racemic form only is stereospecific, the meso form is generally removed by separation from the rac/meso mixtures obtained from the metallocene synthesis.

Thus, for example, in U.S. Pat. No. 4,769,510 it is described the use of rac-ethylene-bis(indenyl)zirconium dichloride and of rac-ethylene-bis(4,5,6,7-tetrahydroindenyl)zirconium dichloride in combination with methylalumoxane for the preparation of isotactic polypropylene.

As regards the stereorigid metallocene compounds of the above type in their meso isomeric form, in EP-A-643,078 they are used in catalyst systems for the preparation of high molecular weight ethylene polymers.

Inasmuch as the methods for the preparation of the above metallocene compounds generally give a rac/meso mixture, both the racemic and the meso isomeric forms have to be separated from the corresponding undesired form. This is generally done by separation methods such as, for example, fractionated crystallization and extraction with solvents, which are often long, impractical and expensive. Moreover, the desired isomer is not always achievable with a high purity.

WO 95/35333 describes a process for the preparation of ethylene polymers having a broad molecular weight distribution by carrying out the polymerization reaction in the presence of a catalyst comprising a mixture of the racemic and meso isomers of a stereorigid metallocene compound and at least one co-catalyst capable of activating both the racemic form and the meso form of the metallocene compound. Different rac/meso ratios have been used in the working examples.

It is thus highly desirable to be able to prepare stereorigid metallocenes in their pure racemic or meso isomeric form, or in a rac/meso mixture with a fixed rac/meso ratio, without resorting to unpractical separation steps of the undesired isomer.

It has now unexpectedly been found that it is possible to selectively decompose one of the isomers of bridged chiral metallocenes in the presence of compounds having either acidic hydrogens or reactive halogen atoms.

Therefore, according to a first aspect, the present invention provides a process for the modification of the rac/meso ratio in a mixture of racemic and meso isomeric form of a stereorigid, bridged metallocene compound of a transition metal selected from those belonging to groups 3, 4, 5 or 6 or to the lanthanides or the actinides in the Periodic Table of the Elements (new IUPAC version), said process comprising contacting said mixture with a decomposition agent selected from the compounds having either an acidic hydrogen atom or a reactive halogen atom for a time sufficient to decompose at least part of one of the isomeric forms.

Depending on the type and concentration of the decomposition agent employed, as well as on the conditions in which the process is carried out, it is possible to control the degree of decomposition of the undesired isomer and, consequently, to prepare rac/meso mixtures enriched in one of the isomers or to prepare the desired isomer substantially free of the undesired isomer.

Inasmuch as the preparation of a stereorigid metallocene compound substantially free of one of its racemic or meso isomeric forms is particularly desirable, in an embodiment of the invention the conditions of the process are selected such that substantially all the undesired isomer is decomposed.

Therefore, according to another aspect, the present invention provides a process for the preparation of the racemic or meso isomeric form of a stereorigid, bridged metallocene compound of a transition metal selected from those belonging to groups 3, 4, 5 or 6 or to the lanthanides or the actinides in the Periodic Table of the Elements (new IUPAC version), said process comprising contacting a rac\meso isomeric mixture of the metallocene with a decomposition agent selected from the compounds having either an acidic hydrogen atom or a reactive halogen atom for a time sufficient to decompose substantially all the undesired isomer.

Non limitative examples of compounds having acidic hydrogen atoms which can be used in the process of the present invention are:

water, alcohols such as methanol, ethanol and the like, organic and inorganic acids such as hydrochloric acid, acetic acid, p-toluen-sulphonic acid, $HB(phenyl)_4$, primary or secondary amines of the formula $RNH_2$ or $R_2NH$ wherein R is an alkyl or aryl group such as diethylamine and the like, quaternary ammonium salts of the formula $(R_pNH^+_{4-p})_q$ $(X^{q-})$, wherein p is 1, 2 or 3, q is 1 or 2, R is an alkyl group and X is a counteranion such as an halogen atom, a $SO_4^{2-}$, $HSO_4^-$, $CO_3^{2-}$, $HCO_3^-$ or $B(phenyl)_4^-$ group.

Non limitative examples of compounds having reactive halogen atoms which can be used in the process of the present invention are the chlorides such as those of the formula $R'_3SiCl$, $R'_3GeCl$ or $R'_3SnCl$ wherein R' is an alkyl group.

In order to reduce the time required for the decomposition, the above described decomposition agents are generally used in a molar ratio with the metal of the undesired metallocene isomer higher than 1:1.

A class of stereorigid, bridged metallocene compounds which are normally obtained as a rac/meso mixture and can thus be subjected to the process of the present invention are those of the formula (I):

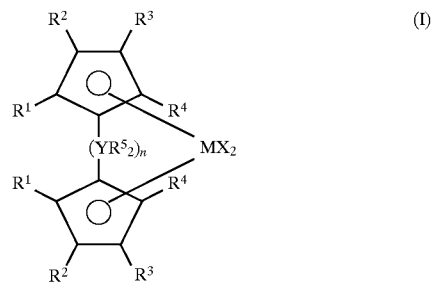

wherein M is a metal selected from Ti, Zr and Hf;

the X substituents, same or different, are hydrogen atoms, halogen atoms or R, OR, SR, $NR_2$ or $PR_2$ groups, wherein the R substituents are $C_1$–$C_{20}$-alkyl, $C_3$–$C_{20}$- cycloalkyl, $C_2$–$C_{20}$-alkenyl, $C_6$–$C_{20}$-alkylaryl, $C_7$–$C_{20}$-alkylaryl or $C_7$–$C_{20}$-arylalkyl radicals which can contain silicon or germanium atoms;

on each cyclopentadienyl group, the $R^1$, $R^2$, $R^3$ and $R^4$ substituents, same or different, are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals and can contain Si or Ge atoms, and moreover two of the $R^1$, $R^2$, $R^3$ and $R^4$ substituents adjacent on the same cyclopentadienyl ring can form a cycle comprising from 5 to 8 carbon atoms, with the proviso that, in at least one cyclopentadienyl group, $R^1$ is different from $R^4$ or $R^2$ is different from $R^3$;

Y is a carbon, silicon or germanium atom;

the $R^5$ substituents, same or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals, and moreover two substituents $R^5$ can form a cycle comprising from 4 to 8 carbon atoms;

n is an integer comprised between 1 and 4, preferably being 1 or 2.

A particularly interesting class of stereorigid, bridged metallocene compounds are the bridged bis-indenyl compounds of the formula (II):

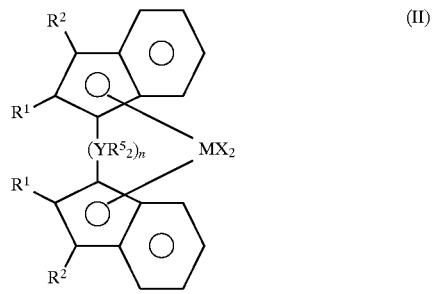

and the corresponding bis-4,5,6,7-tetrahydroindenyl compounds wherein $R^1$, $R^2$, $R^5$, Y, n, M and X are defined as above, and the six-carbon-atom rings of the indenyl ligands can optionally be substituted.

Preferred metallocene compounds of the formulas (I) or (II) are those wherein M is Zr, the X substituents are chlorine atoms or methyl groups, the $(YR^5_2)_n$ bridging group is a $CR^5_2$, $SiR^5_2$ or $(CR^5_2)_2$ group, more preferably a $CH_2$, $C(CH_3)_2$, $Si(CH_3)_2$, or $(CH_2)_2$ group.

A particularly interesting metallocene compound is the ethylenebis(4,7-dimethyl-indenyl)zirconium dichloride which can be easily obtained in its pure meso isomeric form with the process of the present invention.

Therefore, according to a further aspect, the present invention provides a process for the preparation of ethylenebis(4,7-dimethyl-indenyl)zirconium dichloride in its substantially pure meso isomeric form, said process comprising contacting a rac\meso isomeric mixture of said metallocene with a decomposition agent selected from the compounds having either an acidic hydrogen atom or a reactive halogen atom for a time sufficient to decompose substantially all the racemic isomer.

A particularly convenient method for the synthesis of bridged metallocene compounds is described in European Patent Application No. 96100588.1, the relevant parts of which are incorporated in the present description. This method goes through the synthesis of intermediate silyl-, germyl- or stannyl-substituted ligands which can be prepared in their racemic and meso forms, and then can be selectively transformed into the corresponding metallocenes by reaction with a transition metal compound of formula $MX_4$, wherein M is a titanium, zirconium or hafnium atom and X is an halogen atom.

It has been observed that if the rac/meso mixture of the silyl-, germyl- or stannyl-substituted ligand is allowed to react for prolonged times with the transition metal compound, one of the isomers is decomposed.

Therefore, according to a particularly suitable embodiment of the present invention, the decomposition agent is a silyl-, germyl- or stannyl-chloride of the formula $R'_3SiCl$, $R'_3GeCl$ or $R'_3SnCl$, wherein $R'$ is an alkyl group, which is generated by the reaction of a silyl-, germyl- or stannyl-substituted ligand of the target metallocene with a transition metal compound of formula $MX_4$ wherein M is a titanium, zirconium or hafnium atom, preferably a zirconium atom, and X is an halogen atom, preferably a chlorine atom.

The metallocene compounds obtainable with the process of the present invention are useable, in combination with a cocatalyst, in the polymerization of olefins.

The following examples are given for illustrative purposes and do not limit the invention.

CHARACTERIZATIONS

The $^1$H-NMR analyses were carried out on a Bruker 200 MHz instrument, using $CDCl_3$ as a solvent, at room temperature.

All the operations were carried out in a dry nitrogen atmosphere, using the conventional techniques for the handling of compounds which are sensitive to air.

THF=tetrahydrofuran $Et_2O$=ethyl ether

Synthesis of 1,2-bis(1-trimethylsilyl-4,7-dimethyl-indenyl) ethane [EBDMI(TMS)$_2$]

103.8 g (331 mmol) of 1,2-bis(4,7-dimethyl-indenyl) ethane (Boulder, mixture of double bonds positional isomers) were slurred in 680 mL of THF in a 1 L flask equipped with stirring bar. This suspension was added in small aliquots over 30 minutes at room temperature in a 2 L flask equipped with reflux condenser, thermometer and mechanical stirrer, containing 29.48 g of KH (735 mmol) and 205 mL of THF. The reaction was slightly exothermic (T max. 43° C.) with evolution of hydrogen. At the end of the addition the so obtained suspension was stirred for 2 h, obtaining a dark green solution. In a second 2 L flask equipped with thermometer, mechanical stirrer and dropping funnel were placed 93.2 mL of Me$_3$SiCl (734 mmol) and 210 mL of THF. The dark green solution of the potassium salt was added dropwise (2 h, slightly exothermic reaction, T max. 30° C.) and at the end of the addition the mixture was stirred for 44 h, obtaining a brown-orange milk. The reaction was monitored by NMR (40 mg dissolved in CDCl$_3$) and GC. After 16 h the reaction was complete. After 44 h the mixture was treated with water (200 mL) while stirring, and then NaCl to induce phase separation. The organic layer was dried over Na$_2$SO$_4$, filtered and brought to dryness. 142.8 g of a light brown solid was obtained (yield 94.3%).

EXAMPLE 1 (Comparison)

Synthesis of rac/meso-ethylene-bis(4,7-dimethyl-indenyl)zirconium dichloride 0.908 g of ZrCl$_4$ (PM 233.03 g/mol, 3.9 mmol), 90 mL of CH$_2$Cl$_2$ and 1.787 g of EBDMI(TMS)$_2$ (PM 458.5, 3.9 mmol) were placed in a 100 mL flask equipped with stirring bar. The dark brown suspension was stirred for 2 h, then the reaction stopped by removing all volatiles in vacuo: the brown powder was placed in a frit and washed several times with $Et_2O$ until the $Et_2O$ was light yellow (100 mL) then with $CH_2Cl_2$ and finally dried in vacuo. 0.638 g (35%) of yellow-orange powder were obtained: $^1H$ NMR shows the presence of a mixture of the two isomers of $EBDMIZrCl_2$ (rac:meso=45:55). The product was chemically pure.

EXAMPLE 2

Synthesis of meso-ethylene-bis(4,7-dimethyl-indenyl)zirconium dichloride 0.75 g of $ZrCl_4$ (PM 233.03 g/mol, 3.22 mmol), 85 mL of $CH_2Cl_2$ and 1.47 g of $EBDMI(TMS)_2$ (PM 458.5, 3.22 mmol) were charged in a 100 mL flask: a dark brown suspension was obtained which was stirred for 22 h at room temperature. 2 mL aliquots were taken out after 4 and 10 h. The aliquots were dried and analyzed by $^1H$ NMR. After 4 h the reaction was completed (all ligand consumed), with formation of a ca. 1:1 rac/meso with notable decomposition. After 10 h the racemic isomer was diminished, and decomposition increased. After 22 h the reaction was stopped by removing all volatiles in vacuo. The brown powder was transferred on a frit and washed with $Et_2O$ (5×20 mL). After drying a yellow-green powder was obtained (0.364 g, 24%) which analyzes ($^1H$ NMR) as meso-$EBDMIZrCl_2$ ($\geq 98\%$).

EXAMPLE 3

Synthesis of meso-ethylene-bis(4,7-dimethyl-indenyl)zirconium dichloride 5.6 g of $ZrCl_4$ (PM 233.03 g/mol, 24 mmol), 220 mL of $CH_2Cl_2$ and 11 g of $EBDMI(TMS)_2$ (PM 458.5, 24 mmol) were charged in a 250 mL flask equipped with stirring bar. A dark brown suspension was obtained, which was stirred at room temperature for 23 h. The reaction was stopped by filtration, and the residue was extracted with $CH_2Cl_2$ until colourless (the insoluble residue was discarded). The $CH_2Cl_2$ solutions were combined and brought to dryness under vacuum, yielding a brown powder which was placed in a frit and washed several times with $Et_2O$ until the $Et_2O$ was colourless (200 mL). A dark yellow powder was obtained. A fraction of it was washed with $CH_2Cl_2$: $^1H$ NMR analysis revealed the presence of pure meso-$EBDMIZrCl_2$ (the rac isomer being present in traces). The rest of the product contained, besides traces of the rac isomer, also some organic impurities: $Et_2O$ alone was not enough to purify the product. Total yield 2.67 g, 24%. The meso-$EBDMIZrCl_2$ only was obtained, as a lemon yellow powder.

EXAMPLE 4

Synthesis of meso-ethylene-bis(4,7-dimethyl-indenyl)zirconium dichloride 1.53 g of $ZrCl_4$ (PM 233.03 g/mol, 6.54 mmol), 100 mL of $CH_2Cl_2$ and 3 g of $EBDMI(TMS)_2$ (PM 458.5, 6.54 mmol) were placed in a 250 mL flask equipped with stirring bar. The dark brown mixture was stirred 23 h at room temperature. The reaction was stopped by removing the volatiles under vacuum: the brown powder was placed in a frit and washed several times with $Et_2O$ until the $Et_2O$ was colourless (100 mL). A yellow-green powder (0.7 g, 23%) was obtained, which contained meso-$EBDMIZrCl_2$ (rac isomer traces) and organic impurities.

EXAMPLE 5

Meso-enrichment of a 1:1 rac/meso-mixture of ethylene-bis(4,7-dimethyl-indenyl) zirconium dichloride with $H_2O$ 0.25 g of a 1:1 rac/meso mixture of ethylene-bis(4,7-dimethyl-indenyl) zirconium dichloride were dissolved in 55 mL of THF in a 50 mL Schlenk tube under nitrogen, 47 microliters of water were added with a syringe ($Zr/H_2O=5$ molar), and the solution was stirred for 4 hours. Half of the solution was taken out, dried at 30° C. for 5 hours. The solid product was analyzed by $^1H$ NMR (CDCl3, 200 Mhz): meso/rac ratio=90:10. The rest of the solution was stirred for a total of 24 hours, and analyzed in the same way: meso/rac ratio=100:0.

EXAMPLE 6

Meso-enrichment of a 1:1 rac/meso-mixture of ethylene-bis(4,7-dimethyl-indenyl) zirconium dichloride with $CH_3OH$ 0.25 g of a 1:1 rac/meso mixture of ethylene-bis(4,7-dimethyl-indenyl) zirconium dichloride were dissolved in 55 mL of $CH_2Cl_2$ in a 50 mL Schlenk tube under nitrogen, methanol was added with a syringe ($Zr/CH_3OH=5$ molar), and the solution was stirred for 4 hours. Half of the solution was taken out, dried at 30° C. for 5 hours. The solid product was analyzed by $^1H$ NMR (CDCl3, 200 Mhz): meso/rac ratio=60:40. The rest of the solution was stirred for a total of 24 hours, and analyzed in the same way: meso/rac ratio= 60:40.

EXAMPLE 7

Meso-enrichment of a 1:1 rac/meso-mixture of ethylene-bis(4,7-dimethyl-indenyl) zirconium dichloride with $(CH_3)_3SiCl$ 0.25 g of a 1:1 rac/meso mixture of ethylene-bis(4,7-dimethyl-indenyl) zirconium dichloride were dissolved in 55 mL of $CH_2Cl_2$ in a 50 mL Schlenk tube under nitrogen, trimethylchlorosilane was added with a syringe ($Zr/(CH_3)_3SiCl=5$ molar), and the solution was stirred for 24 hours, and analyzed by $^1H$ NMR (CDCl3, 200 Mhz): meso/rac ratio=2:1.

We claim:

1. A process for the modification of the rac/meso ratio in a mixture of racemic and meso isomeric forms of a stereorigid, bridged metallocene compound of a transition metal selected from those belonging to groups 3, 4, 5, or 6 or to the lanthanides or the actinides in the Periodic Table of the Elements (new IUPAC version), the process comprising contacting the mixture with a decomposition agent selected from the compounds having either an acidic hydrogen atom or a reactive halogen atom for a time sufficient to decompose at least part of the racemic form.

2. A process for the preparation of the meso isomeric form of a stereorigid, bridged metallocene compound of a transition metal selected from those belonging to groups 3, 4, 5, or 6 or to the lanthanides or the actinides in the Periodic Table of the Elements (new IUPAC version), the process comprising contacting a rac/meso isomeric mixture of the metallocene with a decomposition agent selected from the compounds having either an acidic hydrogen atom or a reactive halogen atom for a time sufficient to decompose substantially all of the racemic isomer.

3. The process according to claim 1, wherein the compound having a reactive halogen atom is selected from the group consisting of chlorides.

4. The process according to any of claims 1 or 2, wherein the decomposition agent is used in a molar ratio with the metal of the undesired metallocene isomer higher than 1:1.

5. The process according to any of claims 1 or 2, wherein the metallocene compound is selected between those of the formula (I):

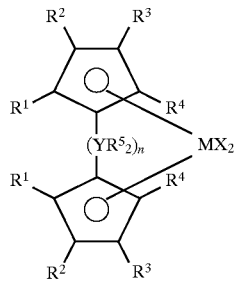

wherein M is a metal selected from Ti, Zr and Hf;

the X substituents, same or different, are hydrogen atoms, halogen atoms or R, OR, SR, $NR_2$ or $PR_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals which can contain silicon or germanium atoms;

on each cyclopentadienyl group, the $R^1$, $R^2$, $R^3$ and $R^4$ substituents, same or different, are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals and can contain Si or Ge atoms, and moreover two of the $R^1$, $R^2$, $R^3$ and $R^4$ substituents adjacent on the same cyclopentadienyl ring can form a cycle comprising from 5 to 8 carbon atoms, with the proviso that, in at least one cyclopentadienyl group, $R^1$ is different from $R^4$ or $R^2$ is different from $R^3$;

Y is a carbon, silicon or germanium atom;

the $R^5$ substituents, same or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals, and moreover two substituents $R^5$ can form a cycle comprising from 4 to 8 carbon atoms;

n is an integer comprised between 1 and 4.

6. The process according to claim 5, wherein the metallocene compound is selected between those of the formula (II):

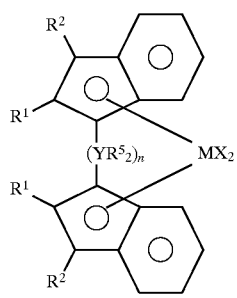

and the corresponding bis-4,5,6,7-tetrahydroindenyl compounds wherein $R^1$, $R^2$, $R^5$, Y, n, M and X are defined as in claim 5, and the six-carbon-atom rings of the indenyl ligands can optionally be substituted.

7. The process according to claim 5, wherein in the metallocene compounds of formula (I) M is Zr, the X substituents are chlorine atoms or methyl groups, the $(YR^5_2)_n$ bridging group is a $CR^5_2$, $SiR^5_2$, or $(CR^5_2)_2$ group.

8. A process for the preparation of ethylenebis(4,7-dimethyl-indenyl) zirconium dichloride in its substantially pure meso isomeric form, said process comprising contacting a rac/meso isomeric mixture of said metallocene with a decomposition agent selected from the compounds having either an acidic hydrogen atom or a reactive halogen atom for a time sufficient to decompose substantially all the racemic isomer.

9. The process according to claim 1, wherein the decomposition agent is a silyl-, germyl-, or stannyl-chloride of the formula $R'_3SiCl$, $R'_3GeCl$, or $R'_3SnCl$, wherein R' is an alkyl group, which is generated by the reaction of a silyl-, germyl-, or stannyl-substituted ligand of the target metallocene with a transition metal compound of formula $MX_4$, wherein M is a titanium, zirconium, or hafnium atom, and X is halogen atom.

10. The process according to claim 1, wherein the compound having an acidic hydrogen atom is selected from the group consisting of water, alcohols, organic acids, inorganic acids, primary or secondary amines of the formula $RNH_2$ or $R_2NH$ wherein R is an alkyl group or aryl group, and quaternary ammonium salts of the formula $(R_pNH^+_{4-p})_q(X)^{q-}$, wherein p is 1, 2, or 3, q is 1 or 2, R is an alkyl group, and X is a counteranion.

11. The process according to claim 10, wherein the compound having an acidic hydrogen atom is selected from the group consisting of methanol and ethanol.

12. The process according to claim 10, wherein the compound having an acidic hydrogen atom is selected from the group consisting of hydrochloric acid, acetic acid, p-toluen-sulphonic acid, and $HB(phenyl)_4$.

13. The process according to claim 10, wherein the compound having an acidic hydrogen atom is diethylamine.

14. The process according to claim 10, wherein the compound having an acidic hydrogen atom is a quaternary ammonium salt having the formula $(R_pNH+_{4-p})_q(X)^{q-}$ wherein p is 1, 2, or 3, q is 1 or 2, R is an alkyl group, and X is a counteranion selected from the group consisting of halogen atoms, $SO_4^{2-}$, $HSO^{4-}$, $CO_3^{2-}$, $HCO_3^-$, or $B(phenyl)_4^-$.

15. The process according to claim 3, wherein the compound having a reactive halogen atom is selected from the group consisting of chlorides having the formula $R'_3SiCl$, $R'_3GeCl$, and $R'_3SnCl$, wherein R' is an alkyl group.

16. The process according to claim 5, wherein n is 1 or 2.

17. The process according to claim 7, wherein the $(YR^5_2)_n$ bridging group is selected from the group consisting of $CH_2$, $C(CH_3)_2$, $Si(CH_3)_2$, or $(CH_2)_2$.

18. The process according to claim 9, wherein M is a zirconium atom.

19. The process according to claim 9, wherein X is a chlorine atom.

20. The process according to claim 9, wherein M is a zirconium atom, and X is a chlorine atom.

* * * * *